United States Patent
Boudjouk et al.

(10) Patent No.: US 7,449,537 B2
(45) Date of Patent: *Nov. 11, 2008

(54) ANTINEOPLASTIC POLYALKOXYALKYLSILOXANES AND METHODS OF USE THEREOF

(75) Inventors: Philip Boudjouk, Fargo, ND (US); Thomas E. Ready, Page, ND (US); Shane Stafslien, Fargo, ND (US); Bhanu P. S. Chauhan, Staten Island, NY (US)

(73) Assignee: NDSU Research Foundation, Fargo, ND (US)

( * ) Notice: Subject to any disclaimer, the term of this patent is extended or adjusted under 35 U.S.C. 154(b) by 1083 days.

This patent is subject to a terminal disclaimer.

(21) Appl. No.: 10/470,012

(22) PCT Filed: Jan. 29, 2002

(86) PCT No.: PCT/US02/01225

§ 371 (c)(1), (2), (4) Date: Jul. 23, 2003

(87) PCT Pub. No.: WO02/060972

PCT Pub. Date: Aug. 8, 2002

(65) Prior Publication Data

US 2004/0077598 A1 Apr. 22, 2004

Related U.S. Application Data

(60) Provisional application No. 60/264,769, filed on Jan. 29, 2001.

(51) Int. Cl.
C08K 77/26 (2006.01)
(52) U.S. Cl. .................. 528/28; 528/29; 528/31; 528/38; 556/425; 556/424
(58) Field of Classification Search .......... 528/28, 528/29, 31, 38; 556/424, 425
See application file for complete search history.

(56) References Cited

U.S. PATENT DOCUMENTS

| | | | |
|---|---|---|---|
| 3,524,900 A * | 8/1970 | Gibbon et al. ........... 525/478 |
| 4,059,581 A | 11/1977 | Prokai | |
| 4,570,010 A | 2/1986 | Stuber et al. | |
| 4,952,715 A | 8/1990 | Blum et al. | |
| 4,973,643 A | 11/1990 | O'Lenick, Jr. | |
| 5,051,458 A | 9/1991 | Costanzi et al. | |
| 5,070,168 A | 12/1991 | O'Lenick, Jr. | |
| 5,128,494 A | 7/1992 | Blum | |
| 5,162,136 A | 11/1992 | Blum et al. | |
| 5,405,655 A | 4/1995 | Blum et al. | |
| 5,639,844 A | 6/1997 | Blum et al. | |
| 5,925,779 A | 7/1999 | Cray et al. | |
| 6,258,968 B1 | 7/2001 | Eversheim et al. | |
| 6,482,912 B2 * | 11/2002 | Boudjouk et al. ........... 528/15 |

FOREIGN PATENT DOCUMENTS

WO  WO 02/060972 A3  8/2002

OTHER PUBLICATIONS

P. Boudjouk, et al., "Nickel Catalyzed Silane Reductions of α, β—Unsaturated Ketones and Nitriles," *Tetrahedron Letters* 39, pp. 3951-3952 (1998), Elsevier Science Ltd., Great Britain.
M. Chauhan, et al., "A New Catalyst for Exclusive β-Hydrosilylation of Acrylonitrile," *Tetrahedron Letters* 40, pp. 4127-4128 (1999), Elsevier Science Ltd., Great Britain.
L. Sommer, et al., "Group VIII Metal Catalyzed Reactions of Organosilicon Hydrides with Amines, Hydrogen Halides, and Hydrogen Sulfide," *J. Org. Chem.* 32, pp. 2470-2472 (1967), American Chemical Society, U.S.A.
R. Corriu, et al., "Selective Catalytic Route to Bifunctional Silanes. Catalysis by Rhodium and Ruthenium Complexes of the Alcoholysis of Diarylsilanes and the Hydrosilylation of Carbonyl Compounds," *J. Chem. Soc.; Chem. Comm.* 1, pp. 38-39 (1973), The Chemical Society, Great Britain.
B. Aylett, et al., "Silicon-Transition-metal Compounds. Part I. Silyltetracarbonylcobalt and Related Compounds," *J. Chem. Soc.*, pp. 1910-1916 (1969), Inorg. Phys. Theor., Great Britain.
B. Aylett, et al., "Silicon-Transition Metal Compounds. Part II. Preparation and Properties of Silylpentacarbonylmanganese," *J. Chem. Soc.*. pp. 1916-1920 (1969), Inorg. Phys. Theor., Great Britain.
B. Aylett, et al., "Silicon-Transition Metal Compounds. Part III. Reactions of Silyltetracarbonylcobalt and Silylpentacarbonylmanganese with Lewis Bases of Nitrogen and Phosphorus," *J. Chem. Soc.; Chem. Comm.*, pp. 1920-1924 (1969), Inorg. Phys. Theor., Great Britain.
B. Sternbach, et al., "The Preparation of Methoxysilanes by the Interaction of Monosilane and Methanol," *J Amer. Chem. Soc.* 81, pp. 5109-5110 (1959), American Chemical Society, U.S.A.
B. Aylett, et al., "A Volatile Silicon-Transition-metal Compound," *J. Chem. Soc.; Chem. Comm.*, p. 217 (1965), The Chemical Society, Great Britain.
Y. Baay, et al., "Trimethyl- and Trichlorosilylcobalt Tetracarbonyls and the Hydrosilation of Ethylene," *Inorg. Chem.* 8 (4), pp. 986-994 (1969), American Chemical Society, U.S.A.
A. Chalk, "Group IV-Cobalt Complexes as Catalysts for Silylation and Cyclic Ether Polymerization," *J. Chem. Soc.; Chem. Comm.*, pp. 847-848 (1970), The Chemical Society, Great Britain.
P. Rakita, et al., "Reductive Solvolysis of Dimethylindenylsilane: Evidence for a Two-step Mechanism," *J. Chem. Soc.; Chem. Comm.*, pp. 533-534 (1973), The Chemical Society, Great Britain.
P. Reddy, et al., "Palladium-Catalyzed Dehydrogenative Polymerization between Hydrosilanes and Quinones or Hydroquinone," *Chemistry Letters*, pp. 250-251 (2000), The Chemical Society of Japan, Japan.

(Continued)

Primary Examiner—Margaret G Moore
(74) Attorney, Agent, or Firm—Foley & Lardner LLP

(57) ABSTRACT

Polyaminofunctional alkoxy polysiloxanes which exhibit antineoplastic activity are disclosed. Pharmaceutical compositions including an effective amount of a polyaminofunctional alkoxy polysiloxane and/or a pharmaceutically acceptable salt thereof are also disclosed. The application also describes methods of suppressing the growth of neoplastic cells and treating neoplastic conditions.

25 Claims, No Drawings

OTHER PUBLICATIONS

Y. Baay, et al., "Synthesis And Properties Of Trimethylsilyl Cobalt Tetracarbonyl And Related Compounds," *Inorg. Nucl. Chem. Letters* 3, pp. 159-161 (1967), Pergamon Press Ltd., Great Britain.

R. Corriu, et al., "Alcoolyse Selective D'Organosilanes Catalysee Par Un Complexe Du Rhodium," *J. Organomet. Chem.* 114, pp. 135-144 (1976), Elsevier Science S.A., The Netherlands.

R. Corriu, et al., "Reactions D'Organosilanes Catalysees Par Des Complexes Du Rhodium; Synthese D'Organosilanes Polyfonctionnels," *J. Organomet. Chem.* 127, pp. 7-17 (1977), Elsevier Science S.A., The Netherlands.

H. Ito, et al., "Highly stereoselective metathesis reaction between optically active hydrosilane and copper(I) salt in 1,3-dimethyl-2-imidazolidinone," *J. Organomet. Chem.* 574, pp. 102-106 (1999), Elsevier Science S.A., The Netherlands.

J. Wang, et al., "Dehydrocoupling reactions of amines with silanes catalyzed by [(Et$_2$N)$_3$U][BPh$_4$]," *J. Organomet. Chem.* 610, pp. 49-57 (2000), Elsevier Science S.A., The Netherlands.

Y. Li, et al., "Efficient Synthesis of Poly(silyl ether)s by Pd/C and RhCl(PPh$_3$)$_3$-Catalyzed Cross-Dehydrocoupling Polymerization of Bis(hydrosilane)s with Diols," *Macromolecules* 32, pp. 6871-6873 (1999), American Chemical Society, U.S.A.

R. Zhang, "Dehydrocoupling Polymerization of Bis-silanes and Disilanols to Poly(silphenylenesiloxane) As Catalyzed by Rhodium Complexes," *Macromolecules* 33, pp. 3508-3510 (2000), American Chemical Society, U.S.A.

Y. Blum, et al., "Modifications of hydrosiloxane polymers for coating applications," *Surface Coatings International Part B: Coatings Transactions* 84 (1), pp. 27-33 (2001), OCCA, U.S.A.

M. Chauhan, et al., "An Efficient Pd-Catalyzed Route to Silyl Esters," *Organic Letters.* 2 (8), pp. 1027-1029 (2000), American Chemical Society, U.S.A.

A. Arruda, et al., "New organosilicon polymer for the extraction and luminescence analysis of uranyl in environmental samples," *Anal. Chim. Acta* 396, pp. 263-272 (1999), Elsevier Science B.V., The Netherlands.

B. Chauhan, et al., "Dehydrogenative condensation of SiH and SH bonds. A metal-catalyzed protocol to stable thiopolysiloxanes," *Tetrahedron Letters* 41, pp. 1127-1130 (2000), Elsevier Science Ltd., The Netherlands.

Q. Fan, et al., "Synthesis and Properties of Polyurethane Modified with Aminoethylaminopropyl Poly(dimethyl siloxane)," *J. App. Polymer Sci.* 74, pp. 2552-2558 (1999), John Wiley & Sons, Inc., U.S.A.

B. Chauhan, et al., "New Neutral Carrier-type Ion Sensors. Crown Ether Derivatives of Poly(methylhydrosiloxane)," *Tetrahedron Letters* 40, pp. 4123-4126 (1999), Elsevier Science Ltd., The Netherlands.

Y. Cai, et al., "Surface properties of silicone-containing block-graft copolymer/polystyrene systems," *J. Adhesion Sci. Technol.* 13 (9), pp. 1017-1027 (1999), VSP, U.S.A.

B. Chauhan, et al., "A Catalytic Route to Grafted Silicones," *Organometallics* 20, pp. 2725-2729 (2001), American Chemical Society, U.S.A.

L. Lestel, et al., "Crosslinking of polyether networks by hydrosilylation and related side reactions," *Polymer* 31, pp. 1154-1158 (1990), Butterworth-Heinemann Ltd., Great Britain.

S. Yun, et al., "Synthesis and Ionic Conductivity of Supramolecular Layered Silicate Hybrids of Phosphotungstates and Poly(ethylene glycol) Dicarboxylates," *Chemistry of Materials* 11 (7), pp. 1644-1647 (1999), American Chemical Society, U.S.A.

T. Ready, et al., "Functionalized Polysiloxanes as Primer Components in Coating Systems," Power Point Slides from Presentation and Abstracts of Presentations, 32$^{nd}$ Great Lakes 2000 Regional Meeting, American Chemical Society, 28 pp. (2000), Fargo, North Dakota, U.S.A.

T. Ready, et al., "New High Performance Polysiloxane Primers for Aluminum," Abstract and Power Point Slides from Presentation to Air Force Office of Scientific Research, 2000 AFOSR Corrosion Review, 26 pp. (2000), Duck Key, Florida, U.S.A.

C. Howie, et al., "Proton Inventory of the Transition State for Hydride Expulsion from Silicon," *J. Amer. Chem. Soc.* 95 (16), pp. 5286-5288 (1973), American Chemical Society, Book and Journals Division, U.S.A.

P. Boudjouk, et al., "Hydrosilylation Catalysed by Activated Nickel," *J. Chem. Soc.; Chem. Comm.*, pp. 1424-1425 (1991), The Chemical Society, Great Britain.

J. Hazziza-Laskar et al., "Biocidal Polymers Active by Contact. IV. Polyurethanes Based on Polysiloxanes with Pendant Primary Alcohols and Quaternary Ammonium Groups," *Journal of Applied Polymer Science* 58, pp. 77-84 (1995), John Wiley & Sons, Inc., New York, NY.

G. Sauvet et al., "Biocidal Polymers Active by Contact. V. Synthesis of Polysiloxanes with Biocidal Activity," *Journal of Applied Polymer Science* 75, pp. 1005-1012 (2000), John Wiley & Sons, Inc., New York, NY.

I. Toukokhonova et al., "Synthesis and Photophysical Properties of Novel Fluorescent Silicones," *Journal of Organometallic Chemistry* 686, pp. 101-104 (2003), Elsevier, London.

R. Resendes et al., "Supramolecular Organometallic Polymer Chemistry: Self-Assembly of a Novel Poly(ferrocene)-*b*-polysiloxane-*b*-poly-(ferrocene) Triblock Copolymer in Solution," *Angewandte Chemie International Edition* 38, No. 17, pp. 2570-2573 (1999), Wiley-Vch Verlag GmbH, Weinheim, Germany.

T. Ready et al., "Facile and Effective Synthesis of Siloxane-Based Polyamines," *Macromolecular Rapid Communications* 22, No. 8, pp. 654-657 (2001), Wiley-Vch Verlag GmbH, Weinheim, Germany.

* cited by examiner

ANTINEOPLASTIC POLYALKOXYALKYLSILOXANES AND METHODS OF USE THEREOF

BACKGROUND

In theory, drugs for the treatment of cancer and tumors should have the capability to accomplish several key goals. First, the drug generally should be able to reach the area of the body where the disease/tumor resides (e.g., brain, lung, breast). The drug should preferably be able to "target" diseased cells (i.e., differentiate between normal cells and diseased cells). The drug should also generally be able to be to transverse various cellular membranes and/or to be "uptaken" by the diseased cell in order to interact with the constituents of that cell. The drug should preferably be able to "recognize" a critical disease related entity (DNA/RNA/Protein) and be capable of binding to it in some fashion (i.e. anti-sense, nucleotide base π-stacking intercalation, triplex formation). Finally, the drug should terminate the disease entity's ability to function (grow) either by inhibition or destruction. The majority of cancer drugs currently in use fail, to a significant degree, with respect to one or more of the attributes listed above. In addition, most cancer drugs currently in use are effective only against very specific types of cancer (i.e. "taxol" for ovarian cancer; "cis-platin" against lung, testicular, and neck tumors) and thus have limited applicability. A single drug which has applicability against a wide variety of cancerous cell lines would be a significant addition to the current arsenal of chemotherapeutic drugs.

Through the use of mutant cell lines which did not require polyamines as well and specific enzyme inhibitors, the metabolic cycle for polyamines has been studied. This has led to several important findings; 1) polyamine levels are much higher in rapidly growing cells than in normally growing cells; 2) polyamines are required for cell growth (i.e., when cells are starved of polyamines, growth stops, but growth resumes to normal when exogenous polyamines are added to the cell culture media); 3) when needed, cells can uptake exogenous polyamines to sustain growth; 4) structural analogues of the natural polyamines can also be taken up by cells from the exogenous media to approximately the same degree as the natural polyamines but the structural analogues are not metabolized within the cell; and 5) when polyamine levels become too high in the cell, polyamines are disposed of either by metabolic breakdown of the polyamines or excretion from the cell.

It has been suggested by several researchers that the polyamine metabolic system might be utilized in conjunction with chemotherapeutic protocols. Probably the most intriguing aspect of this suggestion as it relates to drug design is evidenced by recently reported research which demonstrated that: 1) many diseased cells, particularly cancer cells, have higher intracellular concentrations of the natural polyamines than do normal cells; 2) cells which have higher intracellular concentrations of the natural polyamines take up polyamines in the exogenous media to a much higher degree; and 3) some structural analogues of natural polyamines are taken up by cells from the exogenous media to approximately the same degree as the natural polyamines but the structural analogues are not metabolized within the cell. Taking these factors into consideration suggests that polyamines could represent a motif which might be utilized to simultaneously provide a cellular uptake vehicle as well as a cancer cell targeting capability.

SUMMARY

Aminofunctional alkoxy polysiloxane compounds and salts thereof, which exhibit antineoplastic activity, are described herein. The aminofunctional alkoxy polysiloxanes typically includes a poly((polyaminofunctional alkoxy) alkylsiloxane), such as a poly((diaminofunctional alkoxy) alkylsiloxane) compound. The aminofunctional alkoxy polysiloxane can be a linear and/or cyclic polysiloxane. The aminofunctional alkoxy group(s) in the polyalkoxyalkylsiloxane can include primary, secondary and/or tertiary amino functional groups. Particularly suitable examples of the present aminofunctional alkoxy polysiloxane compounds include polyalkoxyalkylsiloxanes containing one or more 1,3-diaminofunctional alkoxy groups and/or 1,2-diaminofunctional alkoxy groups.

The present application also provides compositions which include a polyaminofunctional alkoxy polysiloxane compound and/or a salt thereof. Typically, the compositions include a pharmaceutically acceptable carrier and the polyaminofunctional alkoxy polysiloxane compound and/or a pharmaceutically acceptable salt thereof.

Methods of suppressing the growth of neoplastic cells and treating neoplastic conditions are also described herein. The method of suppressing the growth of neoplastic cells includes contacting the neoplastic cells with an effective amount of a polyaminofunctional alkoxy polysiloxane compound and/or a salt thereof. As used herein, suppression of growth includes conditions where contacting neoplastic cells with a polyaminofunctional alkoxy polysiloxane results in slower growth of the cells, slower proliferation of the cells and/or more rapid death than normal of the cells. Examples of neoplastic cells whose growth can be suppressed by the present polyaminofunctional alkoxy polysiloxane compounds (and/or corresponding salt(s)) include neoplastic forms of lung, breast and central nervous system cells.

Pharmaceutical compositions including an effective amount of a polyaminofunctional alkoxy polysiloxane compound and/or a pharmaceutically acceptable salt thereof can be used to treat neoplasms. Conditions associated with neoplastic forms of lung, breast and central nervous system cells are examples of conditions which may be treated using the present compositions. Patient treatment using the present method involves administering therapeutic amounts of the pharmaceutical composition. As used herein, the terms "treat" and "therapy" and the like refer to alleviation of clinical symptoms, slowing of the progression, prophylaxis, attenuation or cure of existing disease. In addition, the terms "treat" and "therapy" can refer to preventing the recurrence and/or metathesis of neoplastic growth(s). It is desirable to administer the composition in an amount which is effective to suppress the growth of neoplasm cells and, more preferably, to cause neoplastic growths to shrink. As known to those of skill in the art, depending on the particular type of neoplastic condition, the mode of administration of the pharmaceutical composition may vary. In some instances, the composition may injected directly into a tumor while in others, it may be more advantageous to administer the composition intravenously or orally.

DETAILED DESCRIPTION

The present invention relates to compositions that include an aminofunctional alkoxy polysiloxane compound and/or a salt thereof. In many instances, the compositions include a poly((aminofunctional alkoxy) alkylsiloxane) compound and/or a pharmaceutically acceptable salt thereof, together with a pharmaceutically acceptable carrier. The aminofunctional alkoxy polysiloxane compound typically includes a polyaminofunctional alkoxy polysiloxane compound, such as a poly((diaminofunctional alkoxy) alkylsiloxane) compound.

As used herein, the terms "polyaminofunctional alkoxy polysiloxane compound" and "polyaminofunctional alkoxy polysiloxane" are used interchangeably to refer to an alkoxy polysiloxane compound which includes one or more polyaminofunctional alkoxy groups. For the purposes of this application, the term polyaminofunctional alkoxy group refers to groups which include two or more amino groups and encompasses groups resulting from the removal of a hydroxyl hydrogen atom from a polyamino functional alkanol (e.g., —O—CH$_2$CH$_2$NH—CH$_2$CH$_2$CH$_2$NH$_2$), a polyamino functional cycloalkanol, and/or a polyamino functional hydroxy-substituted aryl compounds (e.g., —O—C$_6$H$_4$—CH$_2$CH$_2$NHCH$_2$CH$_2$NH$_2$). As employed herein, the term "aryl" refers to both hydrocarbon and heteroatom-containing aromatic groups. For example, the polyaminofunctional alkoxy group may be an aminofunctional pyridyloxy group (i.e., a group resulting from the removal of the hydroxyl hydrogen atom from an aminofunctional hydroxypyridine).

Amino groups are organic functional groups which contain a basic nitrogen atom. Examples of amino groups include aliphatic amino groups, such as mono-, di- and trialkylamino groups; cycloaliphatic amino groups, such a piperidinyl and piperazinyl groups; aromatic amino groups (i.e, where the basic nitrogen atom is part of an aromatic ring), such as pyridyl groups, pyrimidyl groups and pyrazinyl groups; and aminosubstituted aromatic groups (i.e., where the basic nitrogen atom is directly bonded to an aromatic group), such as aminophenyl groups (e.g., —NH—C$_6$H$_4$— and —C$_6$H$_4$—NR$_2$).

As employed herein, the term "alkoxy group" encompasses functional groups which include an alkyl-OH, cycloalkyl-OH or aryl-OH functional group whether or not the overall group includes an amino functional group, i.e., an aminofunctional alkoxy groups constitute one type of alkoxy group but not all alkoxy groups include a basic nitrogen atom.

As illustrated in formula (I) below, the siloxane subunits may not all contain a polyaminofunctional alkoxy group. Typically, at least a majority and, in many instances, all of the siloxane subunits of the polymer include a polyaminofunctional alkoxy group. Polysiloxanes where not all of the siloxane subunits of the polymer (with the exception of the terminal subunits) include the same group are referred to herein as "polysiloxane copolymers." As used herein, such "copolymers" can have two or more different siloxane subunits. Polysiloxane copolymers can be formed by reacting a mixture of two alcohols, e.g., a mixture of 2-aminoethanol and ethanol, with a polyalkylhydrosiloxane. Generally, the different siloxane subunits are randomly distributed in a polysiloxane copolymer (a "random copolymer"). However, by using appropriate synthetic methods known to those of skill in the art, polysiloxane copolymers in which the different siloxane subunits are present in "blocks" of two or more identical adjacent subunits can also be produced ("block copolymers"). The present polysiloxane copolymers typically have a ratio of siloxane subunits containing a polyaminofunctional alkoxy group to subunits which do not include a polyaminofunctional alkoxy group of at least about 1:4.

As used herein, the terms "diaminofunctional alkoxy polysiloxane compound" and "diaminofunctional alkoxy polysiloxane" are used interchangeably to refer to an alkoxy polysiloxane which includes one or more diaminofunctional alkoxy groups. A diaminofunctional alkoxy group is a polyaminofunctional alkoxy group which includes two organic functional groups each having a basic nitrogen atom.

The present polyaminofunctional alkoxy polysiloxane compound may include linear and/or cyclic aminofunctional alkoxy polysiloxane(s). The average number of alkoxyalkylsiloxane subunits in the polyaminofunctional alkoxy polysiloxane compound can vary. For example, linear forms of the alkoxy polysiloxane compound may include from 2 to about 2,000 siloxane subunits. Linear forms with no more than about 500 subunits and, more desirably, 2 to about 100 subunits are quite suitable for use as antineoplastic agents. Cyclic forms of the alkoxy polysiloxane compound typically include from 3 to about 12 siloxane subunits and cyclic forms with 3 to 6 units are quite suitable.

Examples of suitable linear polyaminofunctional alkoxy polysiloxanes which can have antineoplastic properties include compounds having the formula I:

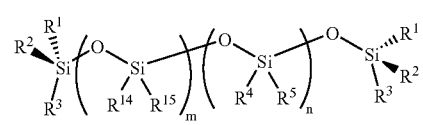

(I)

wherein n is an integer from 2 to 1,000 and m is an integer from 0 to 1,000;

R$^1$, R$^1$ and R$^3$ are independently C$_1$-C$_{10}$ alkyl, cyclopentyl, cyclohexyl, benzyl, toluyl, xylyl or phenyl;

R$^4$ is C$_1$-C$_{10}$ alkyl, cyclopentyl, cyclohexyl, benzyl, toluyl, xylyl or phenyl;

R$^5$ is a polyaminofunctional alkoxy group;

R$^{14}$ is hydrogen, C$_1$-C$_{10}$ alkyl, cyclopentyl, cyclohexyl, benzyl, toluyl, xylyl or phenyl; and R$^{15}$ is C$_1$-C$_{10}$ alkyl, cyclopentyl, cyclohexyl, benzyl, toluyl, xylyl, phenyl, an alkoxy group, or an aminofunctional alkoxy group. Typically, the ratio n/m is at least about 0.25, i.e., at least about 20% of the siloxane subunits include a polyaminofunctional alkoxy group. More commonly, a substantial amount of the siloxane subunits include a polyaminofunctional alkoxy group, e.g., at least about 50% of the subunits include this type of functional group (i.e., the ratio n/m is at least about 1.0). It is often desirable to select aminofunctional polysiloxanes where R$^{14}$ is not hydrogen, e.g., where all of the non-alkoxy substituents on the silicon atoms of the polymer are alkyl, cycloalkyl, benzyl and/or phenyl groups.

Commonly, R$^1$, R$^2$ and R$^3$ are independently C$_1$-C$_6$ alkyl. Linear poly((diaminofunctional alkoxy) alkylsiloxane) compounds in which R$^1$, R$^2$, R$^3$ and R$^4$ are methyl groups are quite suitable for use as neoplastic agents.

Examples of suitable cyclic polyaminofunctional alkoxy polysiloxanes which can have antineoplastic properties include compounds having the formula II:

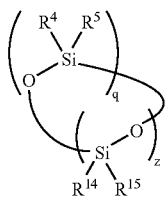

(II)

wherein q is an integer from 1 to 12; z is an integer from 0 to 11; and q+z=an integer from 3 to 12;

$R^4$ is $C_1$-$C_{10}$ alkyl, cyclopentyl, cyclohexyl, benzyl, toluyl, xylyl or phenyl;

$R^5$ is a polyaminofunctional alkoxy group;

$R^{14}$ is hydrogen, $C_1$-$C_{10}$ alkyl, cyclopentyl, cyclohexyl, benzyl, toluyl, xylyl or phenyl; and $R^{15}$ is $C_1$-$C_{10}$ alkyl, cyclopentyl, cyclohexyl, benzyl, toluyl, xylyl, phenyl, an alkoxy group, or an aminofunctional alkoxy group. Cyclic polysiloxanes in which q/z is at least 1.0 and, more desirably, at least 2.0 are quite suitable for use as neoplastic agents. It is often desirable to select cyclic aminofunctional polysiloxanes where $R^{14}$ is not hydrogen, e.g., where all of the non-alkoxy substituents on the silicon atoms of the polysiloxane are alkyl, cycloalkyl, benzyl and/or phenyl groups.

The present polyaminofunctional alkoxy polysiloxanes desirably include a 1,3-diaminofunctional alkoxy group and/or a 1,2-diaminofunctional alkoxy group. Suitable examples of such diaminofunctional alkoxy groups include 1,3-diaminofunctional alkoxy groups having the formula (III):

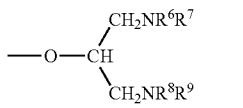

(III)

wherein $R^6$, $R^7$, $R^8$ and $R^9$ are independently hydrogen or $C_1$-$C_6$ alkyl, or $R^6$ and $R^7$ form a $C_3$-$C_8$ cyclic group or $R^8$ and $R^9$ form a $C_3$-$C_8$ cyclic group. Specific examples of such 1,3-diaminofunctional alkoxy groups include

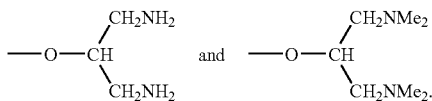

Other examples of suitable polyaminofunctional alkoxy polysiloxanes include a 1,3- and/or 1,2-diaminofunctional alkoxy group having the formula IV:

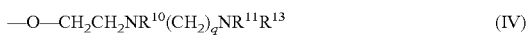

(IV)

where q is 2 or 3; and $R^{10}$, $R^{11}$ and $R^{12}$ are independently hydrogen or $C_1$-$C_6$ alkyl, or $R^{11}$ and $R^{12}$ form a $C_3$-$C_8$ cyclic group. Specific examples of such diaminofunctional alkoxy groups include —O—$CH_2CH_2NHCH_2CH_2NMe_2$,
—O—$CH_2CH_2NHCH_2CH_2CH_2NMe_2$,
—O—$CH_2CH_2NMeCH_2CH_2NMe_2$,
—O—$CH_2CH_2NMeCH_2CH_2CH_2NMe_2$,
—O—$CH_2CH_2NHCH_2CH_2NH_2$, and
—O—$CH_2CH_2NHCH_2CH_2CH_2NH_2$.

The present compositions are useful as antineoplastic agents and are particularly effective at inhibiting the growth and/or killing neoplastic cells and for treating neoplastic pathologies. The polyaminofunctional alkoxy polysiloxanes can be used in pharmaceutical compositions for treatment of neoplastic pathologies. It is anticipated that the pharmaceutical compositions of the present invention can be used to treat a variety of neoplastic conditions. In particular, the present compositions are useful for treatment of conditions associated with neoplastic forms of lung, breast and central nervous system cells.

Polyaminofunctional alkoxy polysiloxanes can be prepared by reacting the corresponding linear polyhydrosiloxane and/or cyclic polyhydrosiloxane with an aminoalcohol. As used herein, the term "aminoalcohol" includes amino functional hydroxy substituted alkyl, cycloalkyl, aralkyl and aryl compounds. The reaction of the polyhydrosiloxane and the aminoalcohol is typically carried out in the presence of a dehydrogenative coupling catalyst, such as those catalysts known to be useful for the dehydrogenative coupling of silanes. Suitable dehydrogenative coupling catalysts include catalysts which have been employed in metal catalyzed dehydrogenative coupling of silanes and alcohols, such as those including Pd, Cu, Mn, Ni, Rh and/or Ru species. Other suitable dehydrogenative coupling catalysts may include Pt, Zn, Ir, Cr, and/or Ti species. The dehydrogenative coupling catalysts may be a mixed metal catalyst that includes more than one metal species. Specific examples of suitable catalysts for the dehydrogenative coupling of silanes and alcohols include the catalysts shown in Table 1 below.

TABLE 1

| | |
|---|---|
| 10% Pd/C | $H_3SiMn(CO)_5$ |
| Cu(O) metal | $Mn_2(Co)_{10}$ |
| CuCl/LiO(t-$C_4H_9$) | Pd/C |
| CuClCN/LiO(t-$C_4H_9$) | $PdCl_2[P(C_6H_5)_3]_3$ |
| CuO(t-$C_4H_9$)/$(C_4H_9)_4$NCl | Raney Ni |
| $RuCl_2[P(C_6H_5)_3]_3$ | |
| tris(dibenzylideneacetone)dipalladium(0)-chloroform | |

Particularly suitable catalysts include rhodium catalysts and, more desirably, catalysts which include rhodium(I) species, such as phosphine-containing rhodium(I) catalysts. Suitable examples of phosphine-containing rhodium(I) catalysts include tris-phosphino rhodium(I) salts, such as RhCl(P($C_6H_5$)$_3$)$_3$ (known as "Wilkinson's catalyst"), RhCl(P($CH_2CH_2(CF_2)_{n=6-8}CF_3$)$_3$)$_3$ and RhCl(P($C_6H_{11}$)$_3$)$_3$. Examples of additional suitable rhodium catalysts include the compounds shown in Table 2.

TABLE 2

| | |
|---|---|
| ($\eta^6$-$C_6H_6B(C_6H_6)_3$)Rh(cod) | Rh(CO)$_2$(acac) |
| (($C_8H_{14}$)$_2$RhCl)$_2$ | Rh(cod)B($C_6H_5$)$_4$ |
| ((RhCl(CH$_2$=CH$_2$)$_2$)$_2$) | Rh($C_8H_{12}$)$_2$BF$_4$/P($C_6H_5$)$_3$ |
| (RhCl$_2$(CO)$_2$)$_2$ | Rh$_2$Co$_2$(CO)$_{12}$ |
| 5% Rh/C | Rh$_4$(CO)$_{12}$ |
| Co$_2$Rh$_2$(CO)$_{12}$ | Rh$_4$(CO)$_{12}$/NEt$_3$ |
| Co$_3$Rh(CO)$_{12}$ | Rh/C |
| Rh/Al$_2$O$_2$ | |

The dehydrogenative coupling reaction between the poly(alkylhydrosiloxane) and the aminoalcohol is commonly carried out under relatively anhydrous, deoxygenated conditions. This may be conveniently achieved by degassing the reaction mixture and carrying the reaction out under an inert gas atmosphere (e.g., under a dry nitrogen or argon atmosphere). The reaction is typically conducted at a temperature of about 60-100° C. over a period of about 1-48 hours. The reaction mixture may initially become yellow in color and emit gas (presumably H₂), and may later become red/orange as the gas emission subsides. Spectroscopic methods, such as NMR and/or IR analysis of the reaction mixture, may be utilized to establish the point at which relatively complete reaction of the Si—H functionalities has been achieved. For example, the reaction progress can be monitored by the residual Si—H and O—H stretches that fall in a convenient window of the IR spectrum. The amount of incorporation of the alcohol into the desired product can also be determined by monitoring NMR signals assigned to specific components.

Examples of reactions which can be used to produce linear poly((aminofunctional-alkoxy)-alkylsiloxane) compounds from varying aminoalcohols ("ROH") and the corresponding linear poly(allylhydrosiloxane) are shown in the following scheme:

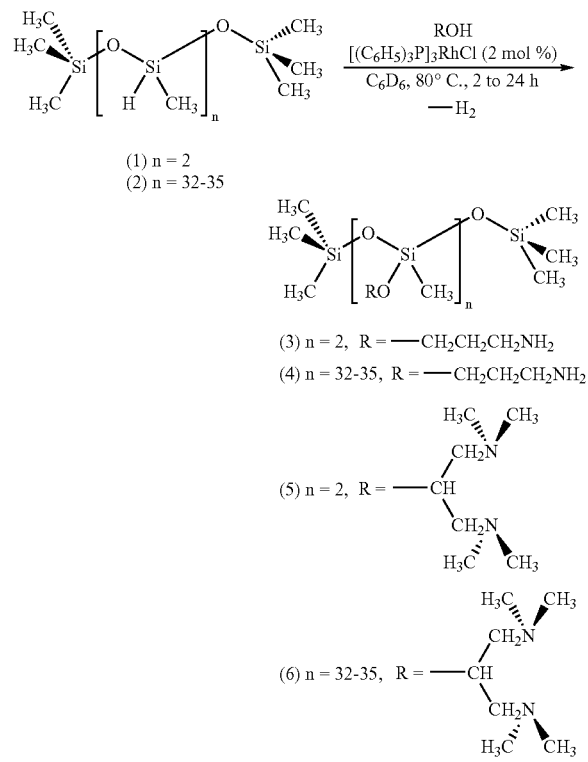

(1) n = 2
(2) n = 32-35

(3) n = 2, R = —CH₂CH₂CH₂NH₂
(4) n = 32-35, R = —CH₂CH₂CH₂NH₂

(5) n = 2, R = —CH(CH₂N(CH₃)₂)(CH₂N(CH₃)₂)

(6) n = 32-35, R = —CH(CH₂N(CH₃)₂)(CH₂N(CH₃)₂)

Similar reactions can be used to produce cyclic poly((aminofunctional alkoxy)-alkylsiloxane) compounds from an aminoalcohol and the corresponding cyclic poly(alkylhydrosiloxane).

The pharmaceutical compositions of the present invention include a polyaminofunctional alkoxy polysiloxanes in effective unit dosage form and a pharmaceutically acceptable carrier. The specification for the dosage unit forms of the polyaminofunctional alkoxy polysiloxanes are dictated by and directly depend on among other factors (a) the unique characteristics of the active material and the particular therapeutic effect to be achieved; (b) the limitations inherent in the art of compounding such active material for the treatment of disease; and (c) the manner of intended administration of the dosage unit form. The principal active ingredient is typically compounded for convenient and effective administration in effective amounts with a suitable pharmaceutically acceptable carrier in dosage unit form as disclosed herein. As used herein, the term "effective unit dosage" or "effective unit dose" is denoted to mean a predetermined amount sufficient to be effective against the neoplastic cells in vivo. Pharmaceutically acceptable carriers are materials useful for the purpose of administering the medicament, which are preferably non-toxic, and can be solid, liquid, or gaseous materials, which are otherwise inert and medically acceptable and are compatible with the active ingredients. The pharmaceutical compositions can contain other active ingredients such as antimicrobial agents, antiviral agents, and other agents such as preservatives.

Water, saline, aqueous dextrose, and glycols are suitable liquid carriers, particularly (when isotonic) for injectable solutions. The carrier can also include various oils, such as those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like. Suitable pharmaceutical carriers and their formulations are described in Martin, "Remington's Pharmaceutical Sciences," 15th Ed.; Mack Publishing Co., Easton (1975); see, e.g., pp. 1405-1412 and pp. 1461-1487. Such compositions will, in general, contain an effective amount of the active compound together with a suitable amount of carrier so as to prepare the proper dosage form for proper administration to the host.

These pharmaceutical compositions can be administered parenterally, including by injection; orally; used as a suppository or pessary; applied topically as an ointment, cream, aerosol, powder; or given as eye or nose drops, etc., depending on whether the preparation is used to treat internal or external viral infections. The compositions can contain 0.1%-99% of the active material. For topical administration, for example, the composition will generally contain from 0.01% to 20%, and more typically 0.5% to 5% of the active material.

The present invention is also drawn to methods of treating neoplastic conditions using the present pharmaceutical compositions. Typically, the compositions will be administered to a patient (human or other animal, including mammals such as, but not limited to, cats, horses and cattle and avian species) in need thereof, in an effective amount to ameliorate the symptoms of the neoplastic condition. It is desirable to administer the composition in an amount which is effective to suppress the growth of the neoplasm and, more preferably, to cause the neoplasm to shrink. The present compositions can be administered by a variety of methods, e.g., orally, intravenously, intramuscularly or topically.

For oral administration, fine powders or granules can contain diluting, dispersing and/or surface active agents, and can be presented in a draught, in water or in a syrup; in capsules or sachets in the dry state or in a non-aqueous solution or suspension, wherein suspending agents can be included; in tablets or enteric coated pills, wherein binders and lubricants can be included; or in a suspension in water or a syrup. Where desirable or necessary, flavoring, preserving, suspending, thickening, or emulsifing agents can be included. Tablets and granules are preferred, and these can be coated. For buccal administration, the compositions can take the form of tablets or lozenges formulated in a conventional manner. For parenteral administration or for administration as drops, as for conditions of the eye, the compounds can be presented in aqueous solution, e.g., in a concentration of from about 0.1 to 10%, more preferably 0.5 to 2.0%, most preferably 1.2% w/v. The solution can contain antioxidants, buffers, and the like.

The compositions according to the invention can also be formulated for injection and can be presented in unit dose form in ampoules or in multi-dose containers with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile, pyrogen-free buffer saline, before use. The present compositions can also be in the form of encapsulated liposomes.

Alternatively, for infections of the eye or other external tissues, e.g., mouth and skin, the compositions are preferably applied to the infected part of the body of the patient as a topical ointment or cream. The compounds can be presented in an ointment, for instance with a water-soluble ointment base, or in a cream, for instance with an oil in water cream base, in a concentration of from about 0.1 to 1% (w/v), more desirably 0.5 to 2.0% (w/v). For topical administration, the daily dosage as employed for adult human treatment will range from 0.1 mg to 1000 mg. However, it will be appreciated that extensive skin conditions may require the use of higher doses.

The present invention may be better understood with reference to the following examples. These examples are intended to be representative of specific embodiments of the invention, and are not intended as limiting the scope of the invention.

EXAMPLES

All reactions were carried out under an atmosphere of argon. Air sensitive products and reagents were handled by standard Schlenk techniques. All solvents were dried and distilled from purple solutions of sodium/benzophenone or $P_2O_5$, and glassware was dried in an oven at 110-120° C. prior to use. Poly(methylhydro)siloxane $Me_3Si$—(O—SiMeH—)$_n$-O—$SiMe_3$ ($M_w$~2000; n=33-35) and RhCl(PPh$_3$)$_3$ (99.99%) were obtained from Aldrich and used as received. Commercially available alcohols were generally used as such without any further purification.

$^{29}$Si, $^{13}$C, $^1$H NMR spectra were recorded on JEOL GSX270 and GSX400 spectrometers. $^1$H and $^{13}$C chemical shifts were measured against Me$_4$Si using solvent resonances as standard locks. $^{29}$Si chemical shifts were referenced to external Me$_4$Si in the same solvent. Molecular weight of the polymers was determined by Waters GPC with polystyrene as standard and THF as solvent. IR spectra were recorded on a Matheson Instruments 2020 Galaxy Series spectrometer as KBr pellets or solutions in CaF$_2$ cells.

Example 1

Deuterobenzene (1 ml), amino alcohol (0.02 mol), and [(C$_6$H$_5$)$_3$P]$_3$RhCl (0.162 g, 0.0002 mol) were introduced to a 25 ml Schlenk tube containing a magnetic stirring bar and sealed with a rubber septum. These components were degassed via 5 freeze/pump/thaw cycles and infused with argon. Linear or cyclic poly(alkylhydrosiloxane) (0.02 mol) was injected into a reaction tube via a syringe while the other reactants were still frozen (to minimize autocatalization by amine moieties) and 5 additional freeze/pump/thaw cycles were performed to further degas the reaction mixture.

At this time, the reaction tube was submerged in a silicon oil bath preheated to 80° C. As all of the reactants became homogenous, the reaction mixture generally turned bright yellow in color and vigorous gas evolution (presumably H$_2$) was observed immediately. The reaction tube was kept under positive argon pressure during the entire course of the reaction in order to flush the H$_2$ gas from the reaction mixture. After approximately one hour, the reaction mixture became red/orange and the gas evolution subsided, the solution was stirred at 80° C. for an additional hour to ensure complete conversion. NMR and IR samples were extracted via a syringe and used to confirm complete conversion.

One of two methods were used to remove the spent catalyst:

Method A:

The reaction mixture was flushed through a 5 ml syringe that contained a Kimwipe plug at the bottom, followed by a 3 ml silica gel plug (neutral, dried under vacuum, and subsequently saturated with either benzene or toluene). On the occasions that excess aminoalcohol was present in the product mixture, it was removed by flushing the product mixture through a silica-gel plug (1 inch×1 cm diameter) with toluene where the aminoalcohol was isolated as a secondary eluant.

Method B:

The reaction mixture was allowed to sit for two days at ambient temperature, after which the catalysts had precipitated out of solution as a red solid. The supernatant was removed from the solid with a syringe.

After using Method A or Method B the catalyst could generally not be detected by NMR in the product solution (catalyst arene substituent $^1$H δ=7.17 m, 7.65 m; $^{13}$C δ=128.92, 129.08, 132.14, 132.60, 132.723). The solvent was then typically removed under reduced pressure.

Example 2

Synthesis of bis-(trimethylsiloxy)-1,3-dimethyl, 1,3-(1,3-(N,N-dimethylamino)-2-propoxy)siloxane, 5

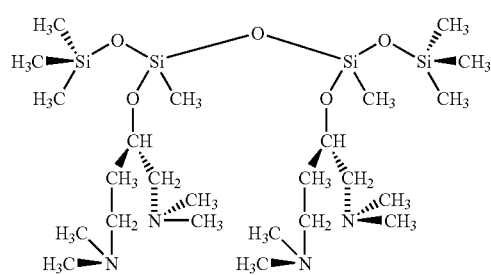

The synthesis was carried out using the general procedure described above in Example 1 with the linear poly(alkylhydrosiloxane), 1,3-bis(trimethylsiloxy)-1,3-dimethylhydrosiloxane 1 (n=2), where 1,3-(N,N-dimethylamino)-2-propanol (3.26 ml, 0.02 mol) was used as the amino alcohol. Method B was used to isolate the desired product 5 (n=2) in 97% yield.

$^1H\square$=0.22 (s, 24H, —OSi(CH$_3$)$_3$), 0.26 (s, 6H, —OSi(CH$_3$)[(CH$_3$)$_2$NCH$_2$CH(—O)CH$_2$N(CH$_3$)$_2$]O—), 2.22 (s, 12H, (CH$_3$)$_2$NCH$_2$CH(—O)CH$_2$N(CH$_3$)$_2$), 2.44 (dm, 4H, (CH$_3$)$_2$NCH$_2$CH(—O)CH$_2$N(CH$_3$)$_2$), 4.15 (p, 1H, (CH$_3$)$_2$NCH$_2$CH(—O)CH$_2$N(CH$_3$)$_2$).

$^{13}$C$\square$=−2.53 (—OSi(CH$_3$)[CH$_3$)$_2$NCH$_2$CH(—O)CH$_2$N(CH$_3$)$_2$]O—), 1.87 (—OSi(CH$_3$)$_3$), 46.55 ((CH$_3$)$_2$NCH$_2$CH(—O)CH$_2$N(CH$_3$)$_2$), 64.32 ((CH$_3$)$_2$NCH$_2$CH(—O)CH$_2$N(CH$_3$)$_2$), 69.99 ((CH$_3$)$_2$NCH$_2$CH(—O)CH$_2$N(CH$_3$)$_2$). $^{29}$Si$\square$=−59.34 & −58.40 (rac & meso diads, —OSi(CH$_3$)[(CH$_3$)$_2$NCH$_2$CH(—O)CH$_2$N(CH$_3$)$_2$]O—), 7.99 & 7.74 (rac & meso diads, —OSi(CH$_3$)$_3$).

Example 3

Synthesis of poly(1,3-N,N-dimethylamino-2-propoxy)methylsiloxane, 6

The synthesis was carried out using the general procedure described above in Example 1 with linear poly(alkylhydrosiloxane) 2 (n=32-35) where 1,3-(N,N-dimethylamino)-2-propanol (3.26 ml, 0.02 mol) was used as the amino alcohol. Method B was used to isolate the desired product 6 (n=32-35) in 97% yield.

$^1H\square$=0.25 (s, 24H, —OSi(CH$_3$)$_3$), 0.38 (s, 6H, —OSi(CH$_3$)[(CH$_3$)$_2$NCH$_2$CH(—O)CH$_2$N(CH$_3$)$_2$]O—), 2.22 (s, 12H, (CH$_3$)$_2$NCH$_2$CH(—O)CH$_2$N(CH$_3$)$_2$), 2.44 (dm, 4H, (CH$_3$)$_2$NCH$_2$CH(—O)CH$_2$N(CH$_3$)$_2$), 4.42 (p, 1H, (CH$_3$)$_2$NCH$_2$CH(—O)CH$_2$N(CH$_3$)$_2$).

$^{13}$C$\square$=−2.72 (—OSi(CH$_3$)[CH$_3$)$_2$NCH$_2$CH(—O)CH$_2$N(CH$_3$)$_2$]O—), 1.87 (—OSi(CH$_3$)$_3$), 46.73 ((CH$_3$)$_2$NCH$_2$CH(—O)CH$_2$N(CH$_3$)$_2$), 64.59 ( (CH$_3$)$_2$NCH$_2$CH(—O)CH$_2$N(CH$_3$)$_2$), 70.02 ((CH$_3$)$_2$NCH$_2$CH(—O)CH$_2$N(CH$_3$)$_2$). $^{29}$Si$\square$=−58.0 to −61.0 (multiple peaks, —OSi(CH$_3$)[(CH$_3$)$_2$NCH$_2$CH(—O)CH$_2$N(CH$_3$)$_2$]O—), 9.21 to 8.92 (multiple peaks, —OSi(CH$_3$)$_3$).

The antineoplastic activity of poly(1,3-N,N-dimethylamino-2-propoxy)methylsiloxane, 6, against several cancer cell lines was examined using the protocol described in Example 7. Aminofunctional alkoxy polysiloxane 6 exhibited antineoplastic activity against the three cancer cells lines tested, Hs578T breast cancer cells, MCF-7 breast cancer cells, and NCI-H460 lung cancer cells. The concentration of polysiloxane 6 required to kill 100% of the cells was 4-32 fold lower for the two breast cancer cell lines than for a normal breast cell line (MCF-12A normal breast cell line).

Example 4

Synthesis of cyclotetra(1,3-N,N-dimethylanzino-2-propoxy)methylsiloxane, 8

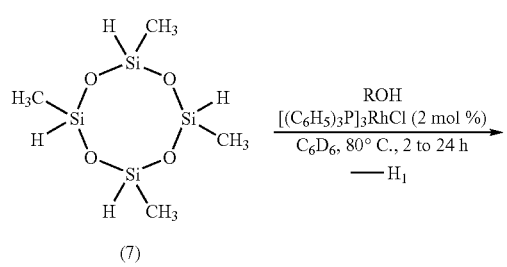

The synthesis was the same as the procedure described above in Example 1 except that cyclotetra(methylhydro)siloxane (7) (1.21 ml, 0.02 mol) was as the cyclic poly(alkylhydrosiloxane) and 1,3-(N,N-dimethylamino)-2-propanol (3.26 ml, 0.02 mol) was used as the amino alcohol. Method B was used to isolate the desired product 8 in 98% yield.

$^1H\square$=0.42 (s, 6H, —OSi(CH$_3$)[(CH$_3$)$_2$NCH$_2$CH(—O)CH$_2$N(CH$_3$)$_2$]O—), 2.22 (s, 12H, (CH$_3$)$_2$NCH$_2$CH(—O)CH$_2$N(CH$_3$)$_2$), 2.47 (dm, 4H, (CH$_3$)$_2$NCH$_2$CH(—O)CH$_2$N(CH$_3$)$_2$), 4.22 (p, 1H, ((CH$_3$)$_2$NCH$_2$CH(—O)CH$_2$N(CH$_3$)$_2$).

$^{13}$C$\square$=−2.37 (—OSi(CH$_3$)[CH$_3$)$_2$NCH$_2$CH(—O)CH$_2$N(CH$_3$)$_2$]O—), 46.98 (CH$_3$)$_2$NCH$_2$CH(—O)CH$_2$N(CH$_3$)$_2$), 64.92 (CH$_3$)$_2$NCH$_2$CH(—O)CH$_2$N(CH$_3$)$_2$), 70.65 (CH$_3$)$_2$NCH$_2$CH(—O)CH$_2$N(CH$_3$)$_2$). $^{29}$Si$\square$=−58.0 to −60.60 (multiple peaks —OSi(CH$_3$)[(CH$_3$)$_2$NCH$_2$CH(—O)CH$_2$N(CH$_3$)$_2$]O—).

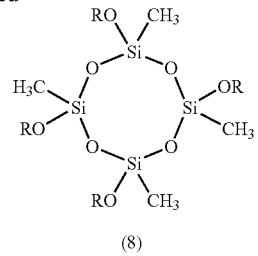

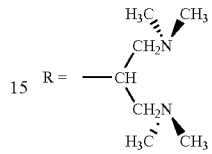

Example 5

Synthesis of bis-(trimethylsiloxy)-1,3-dimethyl-1,3-(3-amino-1-propoxy)siloxane, 3

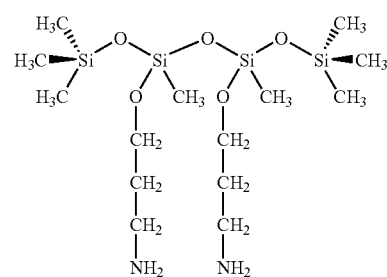

Deuterobenzene (1 ml), 3-amino-1-propanol (1.51 ml, 0.02 mol), and ((C$_6$H$_5$)$_3$P)$_3$RhCl (0.162 g, 0.0002 mol) were introduced to a 25 ml Schienk tube containing a magnetic stirring bar and sealed with a rubber septum. These components were degassed via 5 freeze/pump/thaw cycles and infused with argon. 1,3-Bis(trimethylsiloxy)-1,3-dimethylhydrosiloxane 1 (3.30 ml, 0.02 mol) was injected into the reaction tube via a syringe while the other reactants were still frozen (to minimize autocatalization by the amine moieties) and 5 additional freeze/pump/thaw cycles were performed in order to further degas the reaction mixture.

At this time, the reaction tube was submerged in a silicon oil bath preheated to 80° C. As all of the reactants became homogenous, the reaction mixture became bright yellow in color and vigorous gas evolution (presumably $H_2$) was observed immediately. The reaction tube was kept under positive argon pressure during the entire course of the reaction in order to flush the $H_2$ gas from the reaction mixture. After approximately one hour, the reaction mixture became red/orange and the gas evolution subsided. The solution was stirred at 80° C. for an additional hour to ensure complete conversion. NMR and IR samples were extracted via a syringe and indicated complete conversion.

The reaction mixture was allowed to sit for two days at ambient temperature, after which the catalysts had precipitated out of solution as a red solid. The supernatant was removed from the solid with a syringe. Catalyst could not be detected by NMR in the product solution (catalyst arene substituent $^1H$ δ=7.17 m, 7.65 m; $^{13}C$ δ=128.92, 129.08, 132.14, 132.60, 132.723). The solvent was removed via reduced pressure to produce the desired product 3 (n=2) in an isolated yield of 95%.

$^1H\square$=0.104 (s, 1H, —OSi($CH_3$)$_3$), 0.08 (s, 3H, —OSi($CH_3$)(OCH$_2$CH$_2$CH$_2$NH$_2$)O—), 0.78 (bs, 2H, —OCH$_2$CH$_2$CH$_2$NH$_2$), 1.52 (p, 2H, —OCH$_2$CH$_2$CH$_2$NH$_2$, $J_{2\text{-}1}$=6.35 Hz, $J_{2\text{-}3}$=6.61 Hz), 2.63 (t, 2H, —OCH$_2$CH$_2$CH$_2$NH$_2$, $J_{2\text{-}3}$=6.61 Hz), 3.74 (t, 2H, —OCH$_2$CH$_2$CH$_2$NH$_2$, $J_{1\text{-}2}$=6.35 Hz). $^{13}C\square$=-4.14 (—OSi($CH_3$)(OCH$_2$CH$_2$CH$_2$NH$_2$)O—), 1.43 (—OSi($CH_3$)$_3$), 36.31 (—OCH$_2$CH$_2$CH$_2$NH$_2$), 38.85 (—OCH$_2$CH$_2$CH$_2$NH$_2$), 59.88 (—OCH$_2$CH$_2$CH$_2$NH$_2$). $^{29}Si\square$=-57.74 & -57.77 (rac & meso diads —OSi(CH$_3$)(OCH$_2$CH$_2$CH$_2$NH$_2$)O—), 8.65 & 8.62 (rac & meso diads, —OSi(CH$_3$)$_3$). IR in $C_6D_6$: —NH$_2$ absorbances at 3391 cm$^{-1}$ and 3310 cm$^{-1}$.

Example 6

For the past 10 years, the Developmental Therapeutics Program (DTP) of the National Cancer Institute (NCI) has used an in vitro model consisting of 60 human tumor cell lines as the primary anticancer screen (see, *J. Natl. Cancer Inst.*, 83:757-766, (1991)). An analysis of the data from this screening program has indicated that approximately 95% of the antineoplastic activities from the 60 cell line screen can be identified using only three cell lines. In view of this, the DTP now uses a 3-cell line panel consisting of the MCF7(breast carcinoma) cell line, the NCI-H460 (lung carcinoma) cell line, and the SF-268 (CNS glioma) cell line as its primary anticancer (antineoplastic) assay. This 3-cell line, single-dose assay has been in use by DTP for several years for the evaluation of combinatorial libraries and has proven to be an effective pre-screen for compounds with antineoplastic activity.

In the DTP protocol, each cell line is inoculated and pre-incubated on a microtiter plate. Test agents are then added at a single concentration and the culture incubated for 48 hours. End-point determination are made with sulforhodamine B, a protein-binding dye. Results for each test agent are reported as the percent of growth of the treated cells normalized against the growth of the corresponding untreated control cells, i.e., a reported value of +100% refers to cell growth equivalent to that of the corresponding untreated control cells. Negative percentage refer to treatments which resulted in a smaller number of cells at the end of the test versus the beginning, i.e., a portion of the cells had been killed by the treatment. Compounds which reduce the growth of any one of the cell lines to a value of +32% or less (negative numbers indicate cell kill) are generally considered to be sufficiently "active" to be selected for further evaluation by NCI in a full panel of 60 tumor cell lines over a 5-log dose range.

Two poly((aminofunctional alkoxy)-alkylsiloxane) compounds were tested for antineoplastic activity in the DTP screen. The two compounds (linear poly((aminofunctional alkoxy)-alkylsiloxanes) 5 and 3) were prepared according to the procedures described in Examples 2 and 5 above, respectively. The results of the DTP screen are shown in Table 3 below. The poly((diaminofunctional alkoxy) alkylsiloxane) compound prepared according to the procedure of Example 2 (Compound 5) showed antineoplastic activity against all three test cell lines in the DTP screen. This compound includes 1,3-N,N-dimethylamino-2-propoxy groups. The corresponding analog with 3-amino-1-propoxy groups (Compound 3) was inactive in this DTP screen.

TABLE 3

| | | Growth Percentages | | | |
|---|---|---|---|---|---|
| Compound ID | Sample Concentration | (Lung) NCI-H460 | (Breast) MCF7 | (CNS) SF-268 | Activity |
| Compound 5 (Example 2) | 1.00 E-04 Molar | −16 | −5 | −24 | Active |
| Compound 3 (Example 5) | 1.00 E-04 Molar | | | | Inactive |

Example 7

An additional screening protocol can be used to examine the potential antineoplastic activity of smaple compounds. The chemicals were tested using a Neutral red assay to determine the viability of cells in the culture via a procedure based on that described in Babich et al., *Alternatives to Laboratory Animals* 18:129-144 (1990) and Babich et al., *In Vitro Methods in Toxicology*, Chapter 17, pp. 237-251, Watson RR (ed.) CRC Press, Boca Raton, Fla. (1992). Neutral red dye (3-amino-7-dimethyl-2-methylphenazine hydrochloride) is a water-soluble, weakly basic, spravital dye that accumulates in lysosomes of viable cells. Thus, the relative viability of a culture can be determined by comparing the control cultures to the test cultures. The quantitation of the extracted dye spectrophotometrically has been correlated with the number of viable cells using direct cell counts and protein determinations (see, e.g., Borenfreund et al., *Journal of Tissue Culture Methods* 8:7-9 (1984); and Borenfreund et al., *Toxicology Letters* 24:119-124 (1985)).

Cells to be tested were grown in 150 cm$^2$ flasks in the appropriate medium at 37° C. until confluent. The cells were removed from the flask using trypsin, suspended in a single-cell suspension in appropriate medium, and added to 96-well trays (3 96-well trays per 150 cm$^2$ flask). The cells were incubated at 37° C. for 24 hours, which resulted in a confluent monlayer. Samples of chemicals to be tested were diluted in appropriate medium to 100 ug/ml followed by 10, 1:2 dilutions of each test sample. The medium on the 96-well trays was aspirated. For test samples, 150 ul of each sample dilution were added to each of 8 wells followed by 150 ul of culture medium. The trays were incubated at 37° C.

After 48 hours incubation, the medium was removed from all wells, the cells rinsed once with 200 ul of phosphate buffered saline (pH 7.2), 50 ul of Neutral red stain (40 ug/ul) was added to every well, and the trays incubated at 37° C. Following 3 hours incubation, the neutral red was removed, wells were rinsed with 50 ul of formol/calcium (0.5% formaldehyde and 1.0% calcium), and 200 ul of acetic ethanol (1.0% acetic acid and 50% ethanol) were added. Following 30 minutes at room temperature and rapid agitation for a few seconds, the trays were scanned in a microplate reader (spectrophotometer) at a wavelength of 540-nm.

Titers were determined as the dilution 100% end-point—or the reciprocal of the highest dilution where 100% of the cells were killed, relative to the controls (no test sample).

The invention has been described with reference to various specific and preferred embodiments and techniques. The invention is not to be construed, however, as being limited to the specific embodiments disclosed in the specification. It should be understood that many variations and modifications may be made while remaining within the spirit and scope of the invention.

Statement Regarding Federally Sponsored Research

The U.S. Government has a paid-up license in the present invention and the right (in limited circumstances) to require the patent owner to license others on terms as provided for by the terms of Grant Nos. F49620-96-1-0360 and F49620-99-0283 awarded by the Air Force Office of Scientific Research and Grant No. 9874802 awarded by the National Science Foundation.

What is claimed is:

1. An aminofunctional alkoxy polysiloxane having the formula:

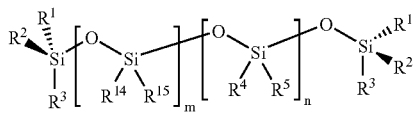

wherein n is an integer from 2 to 1,000; m is an integer from 0 to 1,000; and at least about 20% of the siloxane subunits include a polyaminofunctional alkoxy group;
$R^1$, $R^2$, and $R^3$ are independently $C_1$-$C_{10}$ alkyl, cyclopentyl, cyclohexyl, benzyl, toluyl, xylyl or phenyl;
$R^4$ is $C_1$-$C_{10}$ alkyl, cyclopentyl, cyclohexyl, benzyl, toluyl, xylyl or phenyl;
$R^{14}$ is hydrogen, C1-C10 alkyl, cyclopentyl, cyclohexyl, benzyl, toluyl, xylyl or phenyl;
$R^{15}$ is $C_1$-$C_{10}$ alkyl, cyclopentyl, cyclohexyl, benzyl, toluyl, xylyl, phenyl, or an alkoxy group; and
$R^5$ is

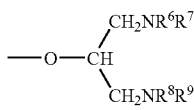

wherein $R^6$, $R^7$, $R^8$, and $R^9$ are independently hydrogen or $C_1$-$C_6$ alkyl, or $R^6$ and $R^7$ form a $C_3$-$C_8$ cyclic group or $R^8$ and $R^9$ form a $C_3$-$C_8$ cyclic group.

2. The polysiloxane of claim 1, wherein m is 0.

3. The polysiloxane of claim 1, wherein m is 0 and n is 2.

4. The polysiloxane of claim 1, wherein m + n is from 2 to about 100.

5. The polysiloxane of claim 1, wherein $R^1$, $R^2$, $R^3$, $R^4$, $R^{14}$ and $R^{15}$ are $C_1$-$C_6$ alkyl.

6. The polysiloxane of claim 1, wherein $R^1$, $R^2$, $R^3$, $R^4$, $R^{14}$ and $R^{15}$ are methyl.

7. The polysiloxane of claim 1, wherein $R^5$ is

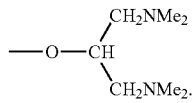

8. The polysiloxane of claim 1, wherein m is 0; n is an integer from 2 to 50; and $R^5$ is

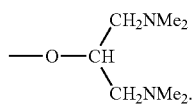

9. The polysiloxane of claim 1, wherein m is 0; $R^1$, $R^2$, $R^3$, $R^4$, $R^{14}$ and $R^{15}$ are methyl; and $R^5$ is

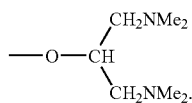

10. The polysiloxane of claim 1, wherein $R^6$, $R^7$, $R^8$, and $R^9$ are $C_1$-$C_6$ alkyl.

11. The polysiloxane of claim 10, wherein $R^1$, $R^2$, $R^3$, $R^4$, $R^{14}$ and $R^{15}$ are methyl.

12. An aminofunctional alkoxy polysiloxane having the formula:

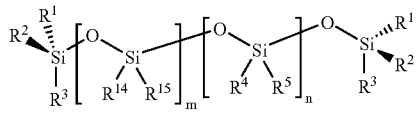

wherein n is an integer from 2 to 1,000; m is an integer from 0 to 1,000; and at least about 20% of the siloxane subunits include a polyaminofunctional alkoxy group;
$R^1$, $R^2$ and $R^3$ are independently $C_1$-$C_{10}$ alkyl, cyclopentyl, cyclohexyl, benzyl, toluyl, xylyl or phenyl;
$R^4$ is $C_1$-$C_{10}$ alkyl, cyclopentyl, cyclohexyl, benzyl, toluyl, xylyl or phenyl;
$R^{14}$ is hydrogen, $C_1$-$C_{10}$ alkyl, cyclopentyl, cyclohexyl, benzyl, toluyl, xylyl or phenyl;
$R^{15}$ is $C_1$-$C_{10}$ alkyl, cyclopentyl, cyclohexyl, benzyl, toluyl, xylyl, phenyl, or an alkoxy group; and
$R^5$ is -O-$CH_2CH_2NR^{10}(CH_2)_q NR^{11}R^{12}$; and q is 2 or 3; and $R^{10}$ is hydrogen or $C_1$-$C_6$ alkyl; and $R^{11}$ and $R^{12}$ are independently $C_1$-$C_6$ alkyl, or $R^{11}$ and $R^{12}$ form a $C_3$-$C_8$ cyclic group.

13. The polysiloxane of claim 12, wherein q is 2.

14. The polysiloxane of claim 12, wherein q is 3.

15. The polysiloxane of claim 12, wherein $R^{10}$ is $C_1$-$C_6$ alkyl; and $R^{11}$ and $R^{12}$ are independently $C_1$-$C_6$ alkyl.

16. The polysiloxane of claim 12, wherein $R^{11}$ and $R^{12}$ are methyl.

17. The polysiloxane of claim 12, wherein $R^5$ is —OCH$_2$CH$_2$NHCH$_2$CH$_2$NMe$_2$.

18. The polysiloxane of claim 12, wherein $R^5$ is —OCH$_2$CH$_2$NMeCH$_2$CH$_2$NMe$_2$.

19. The polysiloxane of claim 12, wherein $R^{10}$ is hydrogen.

20. The polysiloxane of claim 12, wherein $R^{10}$ is methyl

21. The polysiloxane of claim 12, wherein m is 0.

22. The polysiloxane of claim 12, wherein m is 0 and n is 2.

23. The polysiloxane of claim 12, wherein m + n is from 2 to about 100.

24. The polysiloxane of claim 12, wherein the polysiloxane is a random copolymer.

25. The polysiloxane of claim 12, wherein $R^5$ is —OCH$_2$CH$_2$NMeCH$_2$CH$_2$CH$_2$NMe$_2$.

* * * * *